United States Patent [19]

Van Cleve et al.

[11] Patent Number: 5,661,232

[45] Date of Patent: Aug. 26, 1997

[54] CORIOLIS VISCOMETER USING PARALLEL CONNECTED CORIOLIS MASS FLOWMETERS

[75] Inventors: Craig Brainerd Van Cleve, Lyons; Roger Scott Loving, Boulder, both of Colo.

[73] Assignee: Micro Motion, Inc., Boulder, Colo.

[21] Appl. No.: 611,560

[22] Filed: Mar. 6, 1996

[51] Int. Cl.$^6$ .................................................. G01N 11/02
[52] U.S. Cl. .................................. 73/54.05; 73/32 R
[58] Field of Search ............................. 73/54.04, 54.05, 73/54.07, 32 R, 861.351, 861.354, 861.356, 861.357, 861.355

[56] References Cited

U.S. PATENT DOCUMENTS

| | | | |
|---|---|---|---|
| Re. 31,450 | 11/1983 | Smith | 73/861.38 |
| T960,004 | 7/1977 | Neville | 73/54.05 |
| 4,109,524 | 8/1978 | Smith | 73/194 |
| 4,491,025 | 1/1985 | Smith et al. | 73/861.38 |
| 4,680,974 | 7/1987 | Simonsen et al. | 73/861.38 |
| 4,793,191 | 12/1988 | Flecken et al. | 73/861.38 |
| 4,823,614 | 4/1989 | Dahlin | 73/861.38 |
| 4,831,885 | 5/1989 | Dahlin | 73/861.38 |
| 4,854,178 | 8/1989 | Dollfus | 73/861.58 |
| 4,879,910 | 11/1989 | Lew | 73/861.38 |
| 4,882,935 | 11/1989 | Lew | 73/861.38 |
| 4,938,075 | 7/1990 | Lew | 73/861.38 |
| 5,005,400 | 4/1991 | Lew | 73/32 A |
| 5,072,416 | 12/1991 | Francisco, Jr. et al. | 364/571.01 |
| 5,099,697 | 3/1992 | Agar | 73/861.04 |
| 5,226,330 | 7/1993 | Lew | 73/861.37 |
| 5,297,426 | 3/1994 | Kane et al. | 73/202 |
| 5,333,496 | 8/1994 | Fenelon | 73/202 |
| 5,347,874 | 9/1994 | Kalotay et al. | 73/861.38 |
| 5,359,881 | 11/1994 | Kalotay et al. | 73/54.06 |
| 5,448,921 | 9/1995 | Cage et al. | 73/861.38 |
| 5,473,949 | 12/1995 | Cage et al. | 73/861.38 |
| 5,546,814 | 8/1996 | Mattar et al. | 73/861.355 |

OTHER PUBLICATIONS

Insertion vs. In-Line flowmeters: Balancing Accuracy Against Cost; Keith Larson; Jul. 1994; Control.
Bypass Flowmeters; Process Measurement & Analysis, 3rd edition; Bela G. Liptak; Chilton Book Co., pp. 367–371.
Petroleum Engineering Handbook, p. 13.2.

Primary Examiner—Michael Brock
Assistant Examiner—Jay L. Politzer
Attorney, Agent, or Firm—Duft, Graziano, & Forest, P.C.

[57] ABSTRACT

A pair of flowmeters having unequal flow carrying capabilities are effectively connected in parallel to receive a material flow. The material flow through the flowmeters supplies output signals to associated meter electronics which derives mass flow and other information for each meter. The meter electronics is pre-programmed with information regarding the physical characteristics of each flowmeter. The meter electronics uses the pre-programmed information and the derived material flow velocity for each meter and other information to determine the viscosity for the material in the flowmeters.

23 Claims, 4 Drawing Sheets

CORIOLIS VISCOMETER USING PARALLEL CONNECTED CORIOLIS MASS FLOWMETERS

FIELD OF INVENTION

This invention relates to a viscometer that uses parallel connected Coriolis mass flowmeters to derive the viscosity of material flow.

1. Related Application

This application is related to U.S. application Ser. No. 08/587,550 filed on Jan. 17, 1996 in the name of the same inventors of the present application. The disclosure of application No. 08/587,550 is hereby incorporated herein by reference to the same extent as if fully set forth herein.

2. Problems

It is often desirable to determine the viscosity of material flowing in a pipe or conduit. This is done since, in many industrial processes, it is necessary that the flowing material be maintained at a specified viscosity. For example, in an industrial process in which food, such as syrup, or an industrial commodity such as motor oil is processed using a conduit system, it is necessary that the material flowing in the conduit be of a viscosity that enhances its suitability for use by consumers. In other applications, the flowing material must be maintained at a specified viscosity in order for the next step of an industrial process to be accomplished in a specified manner. Another need to know viscosity exists where bypass meters are used to determine the flow rate in a large conduit. The ratio of flow between the meter and the large conduit is a function of viscosity. Therefore, continuously knowing the viscosity enables bypass meters to determine flow rate with improved accuracy.

A common method of deriving viscosity involves human intervention whereby a sample of the flowing material is retrieved and analyzed in order to determine its viscosity. This batch sampling is less than ideal since it involves the expenditure of human labor and is time consuming. It is also undesirable in that it can often involve a shut down of the industrial process while the sample of the flowing material is obtained and analyzed. Furthermore, between samples, the viscosity can vary wildly without detection.

Another method of measuring viscosity is through the use of a commercial viscometer. These instruments are very expensive and generally determine the viscosity by means of a vibrating or rotating member which is inserted into the fluid conduit. While they can measure continually, their expense and the fragility of the vibrating member make them less than ideal.

Vibrating tube Coriolis flowmeters are well known for their ability to measure mass flow, volumetric flow, density, and temperature. Many users of Coriolis flowmeters blend ingredients to achieve a desired viscosity of the material flowing within the flowmeter. A Coriolis mass flowmeter that could also measure viscosity would advantageously provide a continuous process for viscosity determination rather than a discreet batch process involving human intervention and laboratory sampling. Such a viscosity measuring Coriolis mass flowmeter would also eliminate both the expense and the fragility of a separate viscometer. Viscosity measuring Coriolis flowmeters could also be operated on a bypass basis to determine both the flow rate and the viscosity of material flowing in a larger conduit. Knowing the viscosity of the material in the conduit would allow these bypass meters to generate more accurate mass flow output information by compensating for changes in material viscosity.

U.S. Pat. No. 5,359,881 to Kalotay et al., represents an attempt to solve the problems of batch sampling and existing viscometers by providing a Coriolis flowmeter with an internal differential pressure sensor which determines the pressure drop across the flowmeter. From this pressure drop information, the viscosity of the flowing material may be derived. The Kalotay et al., Coriolis flowmeter operates satisfactorily in many applications. However, the Kalotay et al., Coriolis mass flowmeter must be designed to accommodate the differential pressure sensor. This increases its cost and complexity. Also, the Kalotay et al., apparatus is less than ideal for use in certain applications. Due to the mechanical complexities required to accommodate the differential pressure sensor, it cannot be cleaned to the extent required in certain industries such as food processing and pharmaceuticals or in applications wherein the flowmeter apparatus may be used with different materials at different times.

It can be seen that it is a problem to measure the viscosity of material flowing in a conduit by methods that are not time consuming and do not require the use of specialized, expensive, or fragile apparatus. It is furthermore a problem to measure viscosity on a continuous basis in a manner that is sufficiently sanitary for certain applications. Finally, it is a problem to measure flow rate accurately using a bypass configuration without continuously knowing the viscosity so as compensate for the effect of viscosity on meter sensitivity.

SOLUTION

The present invention overcomes the above problems, and achieves an advance in the art by providing a method and apparatus that determines the material viscosity by the use of a pair of parallel connected Coriolis mass flowmeters. The method and apparatus of the present invention determines viscosity by determining the flow velocities of the two parallel connected Coriolis mass flowmeters which have different resistance to material flow. The two flowmeters are connected such that the material inlet pressures are equal to each other as are the material outlet pressures. Each flowmeter generates information representing the mass flow, density, and temperature of the material flowing through it. This information is applied to the microprocessor within the associated electronic apparatus which derives the velocities of the material in the two meters and from the velocities along with the density and flow rates, it calculates the viscosity of the material flowing within the flowmeters and through the conduit to which the flowmeters are connected.

Viscosity calculation is possible because the velocity ratio of the material in two parallel passages of unequal resistance to flow is a function of viscosity, flow rate, and density. (If the resistances to flow of the two flow passages are equal, then the velocities will always be equal and the device will be insensitive to Viscosity.) Standard Coriolis meters determine flow rate and density and then with channel diameter known, they can calculate material velocity. Using two Coriolis meters of unequal resistances to flow then gives the material velocities which are the final pieces of information necessary to calculate material viscosity.

It is known in the art to use Coriolis effect mass flowmeters to measure mass flow and other information for materials flowing through a pipe or conduit. Such flowmeters are disclosed in U.S. Pat. Nos. 4,109,524 of Aug. 29, 1978, 4,491,025 of Jan. 1, 1985, and Re. No. 31,450 of Feb. 11, 1982, all to J. E. Smith et al. These flowmeters have one or more flow tubes of straight or curved configuration. Each flow tube configuration has a set of natural vibration modes which may be of a simple bending, torsional or coupled type. Each flow tube is driven to oscillate at resonance in one of these natural modes. It is further well known that the natural vibration modes of the vibrating tubes are defined in part by the combined mass of the flow tubes and the material flowing within the flow tubes. Therefore, the resonant frequency can be used to determine the density of the material within the tubes.

Material flows into the flowmeter from a connected conduit on the inlet side of the flowmeter, is directed through the flow tube or tubes, and exits the outlet side of the flowmeter. When there is no material flow, all points along the flow tubes oscillate with identical phase due to an applied driver force. With material flow, Coriolis acceleration cause each point along the flow tubes to have a different phase. The phase on the inlet side of the flow tube lags the driver while the phase on the outlet side leads the driver. Sensors are placed on the flow tubes to produce sinusoidal output signals representative of the velocity of the flow tubes. The phase difference between two sensor signals is proportional to the mass flow rate of material through the flow tubes.

Information regarding the characteristics of material flowing in a Coriolis mass flowmeter must be derived with great accuracy since it is often a requirement that the derived flow rate information have an accuracy of at least 0.15% of reading. These flowmeter output signals are sinusoidal and are displaced in time or phase by an amount determined by the Coriolis forces generated by the flowmeter through which the material flows. The signal processing circuitry which receives these sensor output signals measures this time difference with precision and generates the desired characteristics of the flowing process material to the required accuracy of at least 0.15% of reading.

In accordance with a first embodiment of the invention, a pair of Coriolis mass flowmeters are connected in parallel with each other on a full flow basis between a material supply conduit and a material receiving conduit. The two flowmeters, including their material inlets and outlets, have different resistances to the flow of material. This could be due to the flow paths having different cross section areas, lengths, or both. The differing resistance to flow could also be due to a localized restriction such as an orifice plate in one of the flowmeters. The material inlets of the two flowmeters are coupled to the material supply conduit and the material outlets of the two flowmeters are connected to the material receiving conduit. In operation, the two flowmeters provide output signals representing mass flow rate, temperature, and density pertaining to the material flow in each meter. The output information from each meter is delivered to its associated electronic apparatus which processes the received information and calculates the material velocity in each flowmeter. The velocity data from one flowmeter is then transmitted from one meter electronics to the other where the material viscosity is then calculated by a microprocessor in the electronic apparatus. In this first embodiment, the two flowmeters comprise physically separate meters connected in parallel between the supply and receiving conduit. They also have physically separate electronics which are connected only for the transfer of velocity data.

In a second embodiment of the invention, unitary apparatus is provided which comprises the functional equivalent of a pair of parallel connected Coriolis mass flowmeters. In this embodiment, however, many redundant components of the two flowmeters are combined into one. For instance, rather than using separate housings, manifolds, drivers, temperature measuring devices, and electronic apparatus, they are shown combined into one elongated member having two flow tubes for the benefit of reduced cost. The flow tubes can be two tubes of equal length, diameter, stiffness, and mass. Each flow tube has its own independent pair of velocity sensors. The time delay between the signals from the velocity sensors determines the mass flow rate. Independent velocity sensors on each flow tube, enable the mass flow rates and velocities to be determined independently.

In order to determine viscosity, the two parallel flow paths must offer differing resistances to flow. This is achieved by restricting the flow channel between the inlet conduit and one of the flow tubes, and/or restricting the flow channel between the outlet and that same flow tube. Thus, the second embodiment, like the first embodiment, comprises two parallel flow channels of differing resistance to material flow along with the means for determining density and mass flow rate of the flowing material in each channel. The second embodiment also includes an electronic apparatus for calculating the density, material velocities, and viscosity of the material. The second embodiment differs from the first in that it comprises a single structure that can independently measure the flow rates in each of its two tubes each of which is the equivalent of a separate straight tube Coriolis mass flowmeter. Like the first embodiment, the two flow paths offer differing resistance to flow.

In accordance with a third alternative exemplary embodiment of the invention, a pair of physically separate Coriolis mass flowmeters, each of differing resistance to flow, are effectively coupled in parallel to a conduit having a material flow. This configuration, in which only part of the flow is directly measured and the full flow is inferred, is known as a bypass meter configuration. Users of bypass meters traditionally assume that the ratio of flow through the meter to that through the main conduit is constant. Unfortunately, the ratio is dependent on density, viscosity and fluid flow rate.

In this third embodiment, the material inlets of the flowmeters are coupled to the interior of the conduit with the opening of the material inlet of each flowmeter facing upstream to the material flow. The material outlet of each flowmeter is connected downstream in the conduit with the open end of the material outlet extending through the conduit and flush with the inner surface of the conduit. This downstream conduit includes a venturi element internal to the conduit. The venturi generates a low pressure area in the conduit proximate the outlets and, in turn, an increased pressure drop across the two flowmeters. This results in increased material flow through each meter and, in turn, increased meter sensitivity. The two parallel connected flowmeters each generate signals indicative of flow rate and density. The two flowmeters apply their output information to a common meter electronics element which receives the information, derives the mass flow rate and density for each flowmeter and, in turn, calculates the velocities, and the viscosity for the material in the flowmeters. This viscosity along with the density, meter flow rates, and meter geometric information enables an accurate derivation of the flow rate for the material through the entirety of the conduit.

In yet another alternative embodiment, the unitary apparatus comprising two parallel straight tube Coriolis flowmeters of the second embodiment is operated on a bypass basis to determine flow and viscosity information for material in a connected conduit.

DESCRIPTION OF DRAWINGS

These and other advantages and features of the present invention may be better understood from a detail reading of the following detailed description thereof taken in conjunction with the drawings in which.

DETAILED DESCRIPTION

Figure 1:
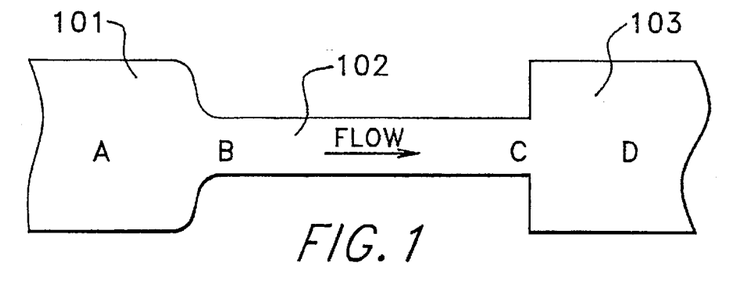
FIG. 1 discloses a flow tube positioned between the two conduits.

Description of FIG. 1

FIG. 1 discloses a conduit 101 which gradually contracts into a conduit 102 of lesser diameter at B. After a short distance, conduit 102 enlarges at C abruptly into a conduit 103 of the same diameter as conduit 101. FIG. 1 will subsequently be used in the derivation of the equation relating viscosity to the other known fluid parameters.

Figure 2:
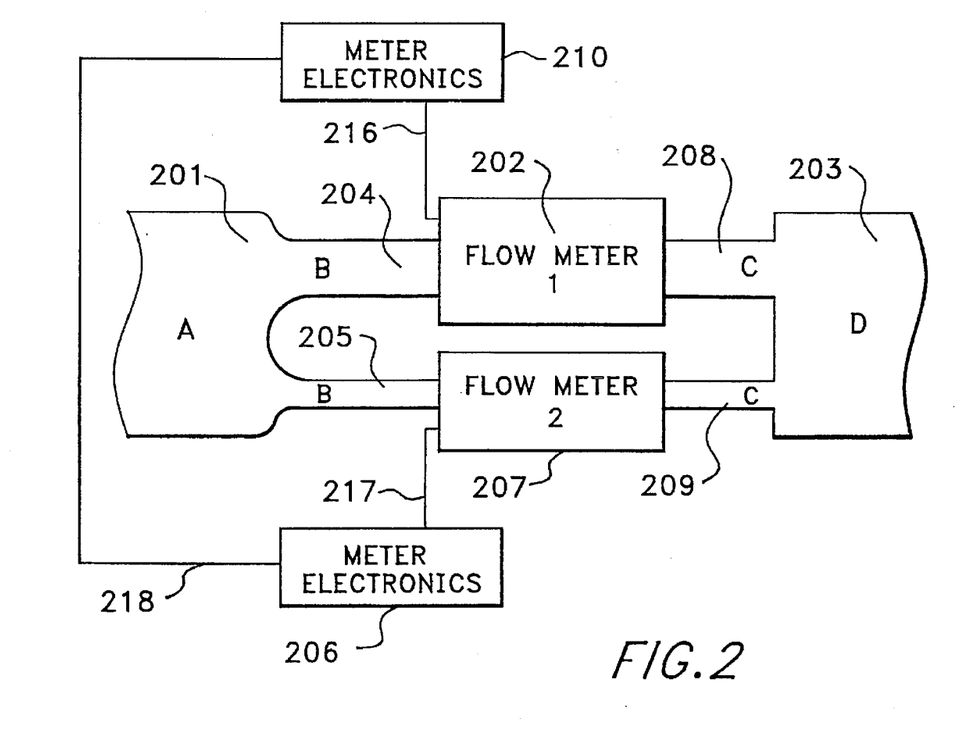
FIG. 2 discloses a pair of Coriolis mass flowmeters connected in parallel between two conduits.

Description of FIG. 2

FIG. 2 discloses a pair of Coriolis mass effect flowmeters 202 and 207 connected effectively in parallel between a supply conduit 201 and a material receiving conduit 203. Inlet 204 of flowmeter 202 is connected to source conduit 201 as is inlet 205 of flowmeter 207. Material outlets 208 and 209 are connected to receiving conduit 203. The two flowmeters, including their inlets and outlets have different resistances to material flow or, are of different dimensions including the cross sectional areas of the inlets and outlets as well as the internal flow tubes of each flowmeter. Paths 216 and 217 comprise the electrical connections between meter electronics 206 and 210 and the drivers and sensors of the two flowmeters.

In operation, meter electronics 210 for flowmeter 202 and meter electronics 206 for flowmeter 207 applies a drive signal over paths 216 and 217 to oscillate the flow tubes of each meter at their resonant frequency with material flowing therethrough. The oscillatory motion of these flow tubes containing flowing material are detected by velocity sensors in each flowmeter. The sensors of each flowmeter supply output information over paths 216 and 217 to meter electronics 206 and 210 representing a time difference or phase shift between the signals detected by each sensor. In a well known manner, meter electronics 210 and 206 use the received sensor signals to derive mass flow rate and density for the material flow within each of their associated flowmeters. Meter electronics 210 applies its derived information over path 218 to meter electronics 206 which then has the derived information for both flowmeters 202 and 207. As is subsequently described in detail, meter electronics 206 then uses the derived mass flow rate and density information for both flowmeters to calculate the velocities of the material in the two meters and thereby to calculate the viscosity of the flowing material. Meter electronics 206 and 210 are well known in the art and may comprise Micro Motion model RFT9739 transmitter units, which may be obtained from Micro Motion, Inc., of Boulder, Colo. 80301. Coriolis flowmeters 202 and 207 may be of any type known in the art and advantageous may comprise the flowmeters disclosed in the aforementioned Smith et al patents. The disclosure of the Smith et al patents are hereby incorporated by reference into the present application to the same extent as fully set forth herein. Flowmeters 202 and 207 may also be model CMF025 or CMF050 flowmeters made and sold by Micro Motion, Inc., of Boulder, Colo. 80301.

Figure 3:
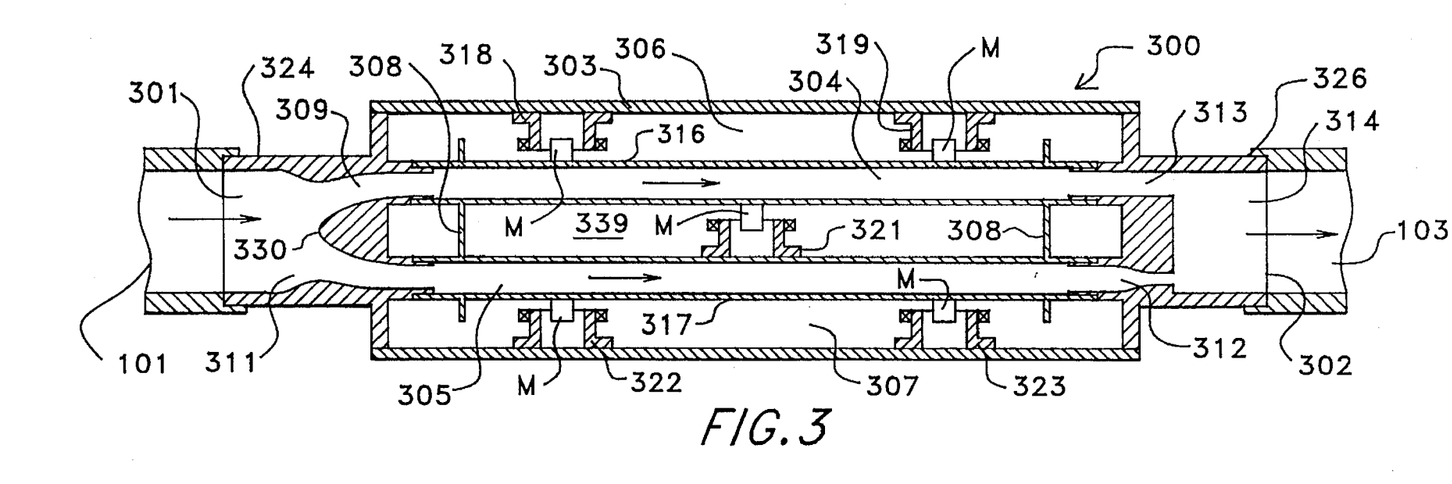
FIG. 3 discloses a unitary element embodying a pair of in line straight tube Coriolis mass flowmeters connected between two conduits.
Figure 4:
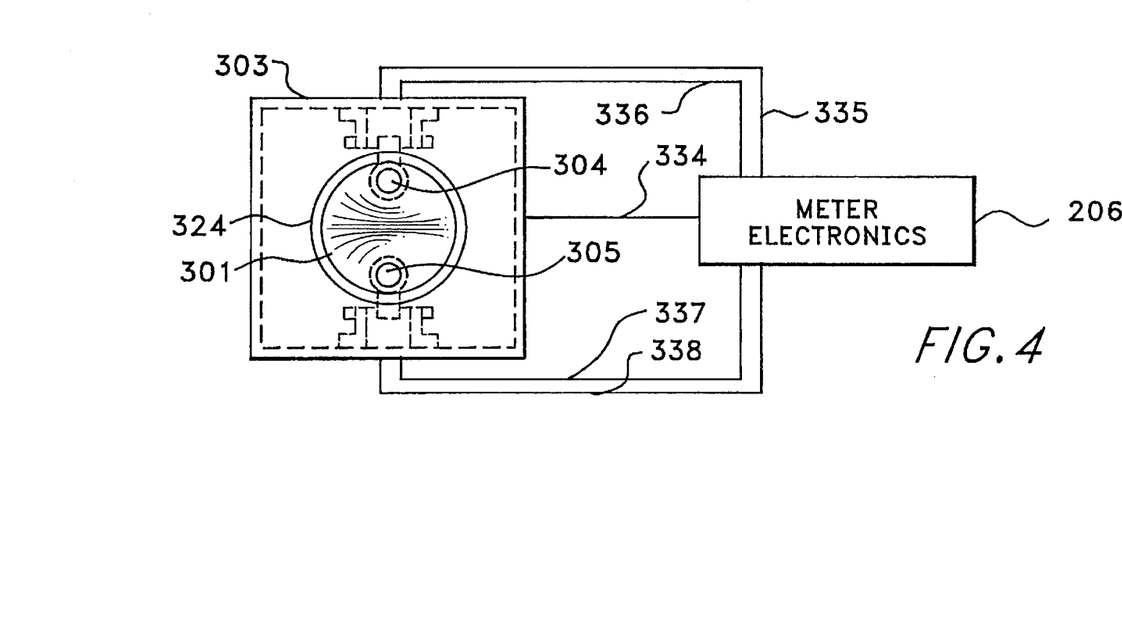
FIG. 4 discloses a cross section end view of the apparatus of FIG. 3.

Description of FIGS. 3 & 4

FIGS. 3 and 4 disclose apparatus 300 which comprises a pair of straight tube Coriolis flowmeters combined into a single apparatus. The first flowmeter comprises flow channel 304 together with its associated coils 318, 319 and magnets M. The second flowmeter comprises flow channel 305 together with its associated coils 322, 323 and magnets M. Flow channels 304 and 305 are parallel to each other. Apparatus 300 has an inlet 301 adapted to receive a material flow from supply conduit 101. Apparatus 300 also has an outlet 314 adapted to deliver material that passes through the flowmeters 304, 305 to a material receiver conduit 103.

Void 339 positioned between flow channels 304 and 305 contains coil 321 and associated magnet M. This coil and magnet combination comprises a driver which, when energized by a drive signal received over path 334 or FIG. 4 from meter electronics 206, oscillates flow channels 304, 305 transversely at their common resonant frequency when material flows therethrough from inlet 301 to output 314. The concurrent oscillation of the flow tube, and the flow of material therethrough causes the flow tubes to function as two straight tube Coriolis flowmeters in which the material in flow tubes 304 and 305 undergoes a Coriolis acceleration whose amplitude is dependent upon the mass flow rate of material through the flow tubes. This acceleration causes a deformation of the flow tubes and a resulting time delay between the signals output by sensor coils 318/319 which comprise the pair of sensors for flow channel 304. The oscillating motion for flow channel 305 is detected by sensor coils 322 and 323. The output signals of sensor coils 318 and 319 are displaced from each other in time by an amount dependent upon the mass flow rate through flow channel 304. The output signals from coils 322 and 323 are also displaced from each other in time by an amount dependent upon the mass flow rate through flow channel 305. These signals are applied over conductors 335, 336, 337, and 338 on FIG. 4 to meter electronics 206 which uses the temporal displacement of each pair of signals to derive information for the material flow rates through flow channels 304/305. The density of the flowing material is derived from the resonant frequency of the vibrating flow channels 304 and 305. Meter electronics 206 then calculates the material velocities and viscosity of the flowing material. Material entering flowmeter apparatus 300 at inlet end 301 is diverted by element 330 so that a portion of the material enters flow channel 304 and while the remainder enters channel 305. The material that enters flow channel 304 exits at orifice 313 where the material enters outlet 314. The material that enters flow channel 305 exits the flow channel through orifice 312. Orifice 312 comprises a constriction which narrows and reduces the cross sectional area through which the material in flow tube 305 must flow before entering outlet 314. Inlets 309 and 311 of flow tubes 304 and 305 are of essentially the same diameter. Likewise, flow tubes 304 and 305 are of essentially the same diameter. The orifice area 312 reduces the effective material flow carrying capability of flow tube 305 as compared to that of flow tube 304. As a result, the flow tubes 304 and 305 have different material flow characteristics including flow velocities. This is an important aspect to the invention and is a necessary part of the process by which meter electronics 206 derives the viscosity for the material flowing in flow channels 304 and 305. If the resistance to flow of the two passages were equal, the material flow velocity ratio would remain constant and would give no indication as to the viscosity of the fluid. It is only by having differing resistances to flow that the material flow velocity ratio changes with viscosity thus enabling the calculation of viscosity.

FIG. 4 is a cross sectional end view of the inlet 301 of structure 300 of FIG. 3. Shown on FIG. 4 are flow channels 304 and 305, outer wall 324 of the inlet portion of flow structure 300 as well as inlet opening 301. Also shown on FIG. 4 are sensor coils 318 and 322 together with their associated magnets M. Conductors 335 and 336 interconnect coils 318 and 319 of flow channel 304 with meter electronics 206. Conductors 337 and 338 interconnect sensor coils 322 and 323 of flow channel 305 with meter electronics 206. One of the functions of meter electronics 206 is to receive output signals from the sensor coils and to measure the time differential between the signals of each sensor coil pair to derive mass flow and density pertaining to the material in flow channels 304 and 305. Another function of the meter electronics includes calculation of the volumetric flow rates and velocities of the flowing material. The meter electronics 206 in FIG. 4 contains all of the separate circuit elements of two separate meter controllers, such as the Micro Motion RFT9739, except that they share common elements such as the power supply, drive circuit, and electronic housing. Viscosity is determined by meter electronics 206 from the mass flow rate and density derived for each flow channel from the geometric parameters of flow channels 304 and 305 which are entered into a ROM portion of the meter electronics micro processor and from the ratio of material flow velocities in the two flow tubes. This is shown in equation 21.

Figure 5:
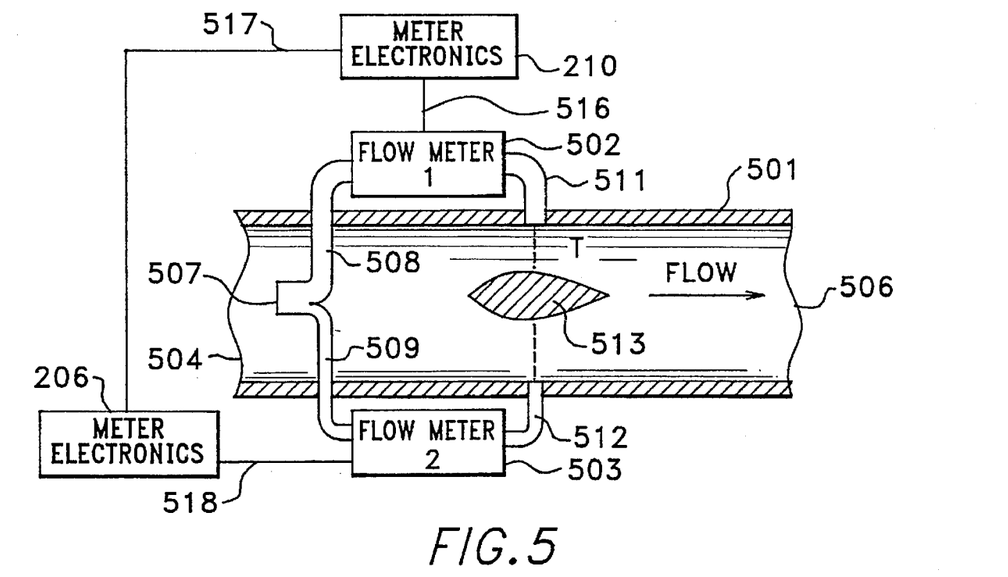
FIG. 5 discloses a pair of separate Coriolis mass flowmeters having their inlet and outlets coupled to a conduit on a bypass basis.

Description of FIG. 5

FIG. 5 discloses an alternative exemplary embodiment of the invention comprising a pair of flowmeters 502 and 503 effectively connected in parallel and operating on a bypass manner to measure flow information including the viscosity of material flowing through conduit 501. Flowmeters 502 and 503 have a common inlet 507 which diverges into inlet 508 for flowmeter 502 and inlet 509 for flowmeter 503. Element 511 is the material outlet for flowmeter 502 and element 512 is the material outlet for flowmeter 503. The two flowmeters have different resistance to material flow and therefore different flow carrying capacities since the cross-sectional flow area of the inlet and outlet and flow tubes for flowmeter 502 is different than that of the inlet and outlet and flow tubes for flowmeter 503. The opening of inlet 507 faces upstream so that it receives both the static and dynamic pressure of the material flow within conduit 501. The ends of material outlets 511 and 512 are flush with the inner surfaces of conduit 501 proximate the portion of the conduit designated as T which comprises of the throat of the venturi formed by structure 513 positioned within the interior of conduit 501. The venturi 513 increases the velocity of the flowing material while reducing the material pressure at the venturi throat T. This reduced pressure causes a sizeable pressure drop between the inlet 507 and outlet 511/512 of the two flowmeters. This pressure drop results in increased flowmeter sensitivity.

Conductors 516 and 518 are the circuit paths over which meter electronics 210 and 206 apply a drive signal to oscillate the flow tubes of each flowmeter as well as the conductors over which the flowmeters supply the output signals from their sensors. The output signals enable the meter electronics 210 and 206 to derive mass flow rate and other information for each flowmeter in the same manner described in connection with embodiment of FIGS. 2 and 3. The ROM, RAM and the micro processor of meter electronics 206 are programmed with information such as the physical parameters of the two flowmeters, the conduit as well as the venturi throat. Meter electronics 206 also receives derived information over path 517 from meter electronics 210. Meter electronics 206 uses this information including derived the mass flow rate that for each flowmeter and, based upon the fact that the two flowmeters am subject to equal pressure drops, the meter electronics 206 derives the viscosity for the flowing material using the material flow velocity ratio between the two flowmeters. It further derives with the ratio of the material flowing in the flowmeters to that of the material flowing within conduit 501. From this, the mass flow rate within the conduit 501 is determined as described in detail in the above identified co-pending U.S. application Ser. No. 08/587,550. Coriolis mass flowmeters 502 and 503 may advantageously be of the type shown in the aforementioned Smith et al patents. They may also be model CFM025 of CFM050 flowmeters made and sold by Micro Motion, Inc., of Boulder, Colo. 80301.

Figure 6:
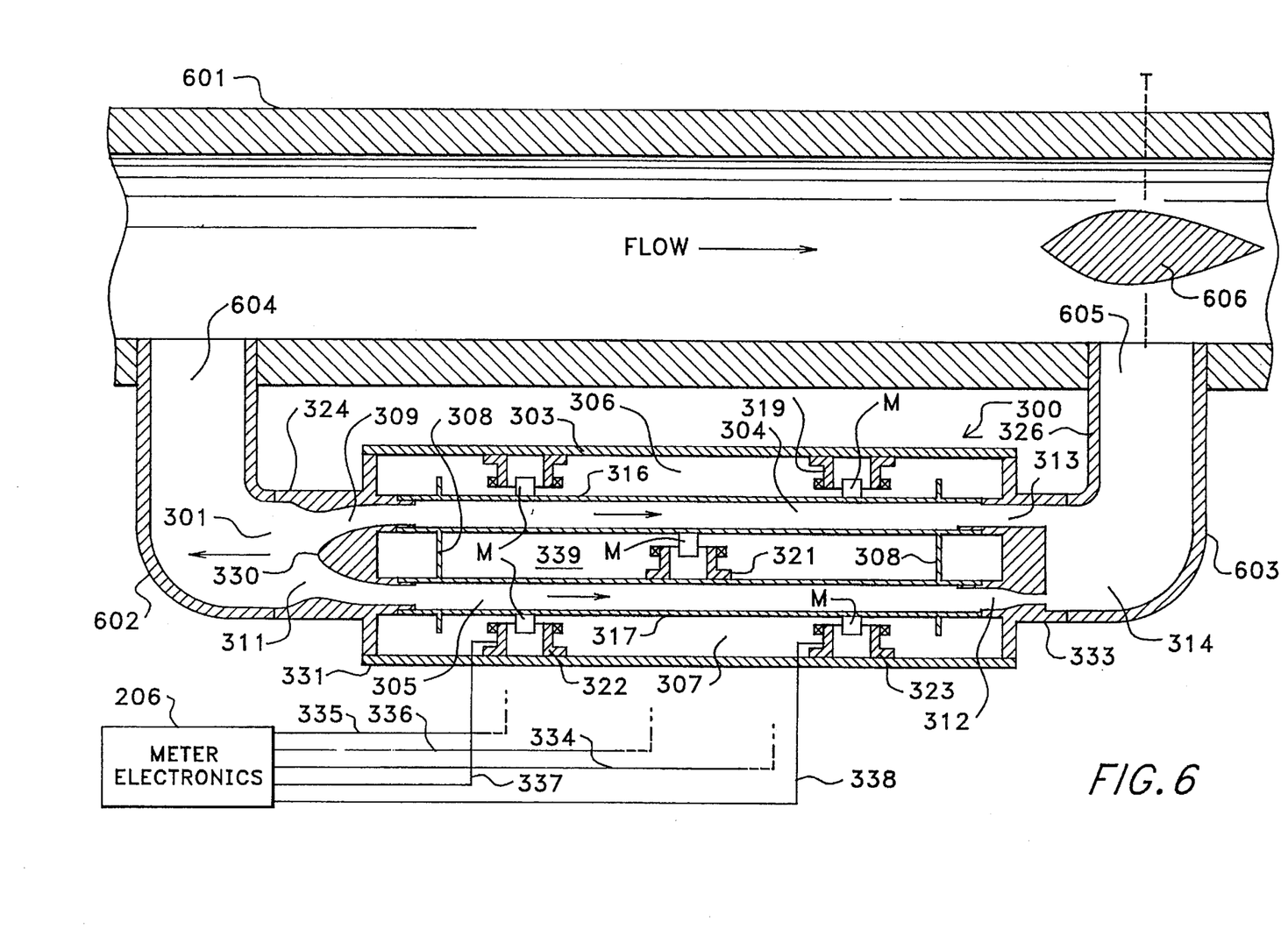
FIG. 6 discloses the Coriolis mass flowmeters of FIG. 3 connected on a bypass basis to a conduit.

Description of FIG. 6

FIG. 6 shows the apparatus 300 of FIG. 3 connected on a bypass basis to a conduit 601. Inlet 301 is connected by tube 602 to opening 604 in the wall of conduit 601. Outlet 314 is connected by tube 603 to an opening 605 in the wall of conduit 601. Element 606 creates a venturi having a throat T proximate opening 605. Since the material pressure at T is much lower than that upstream at 604, the flow apparatus and its flow channels 304 and 305 are subject to a sizeable pressure drop as material flows downstream in conduit 601. The flow channels 304/305 of FIG. 6 operate in the same manner as those of FIG. 4, together with meter electronics 206 to derive the viscosity and mass flow rate on a bypass basis for the material flow in conduit 601 as described for FIG. 5. Meter electronics 206 of FIG. 6 is a dual unit as described for FIG. 4 that derives material flow information for both flow channels 304 and 305.

Figure 7:
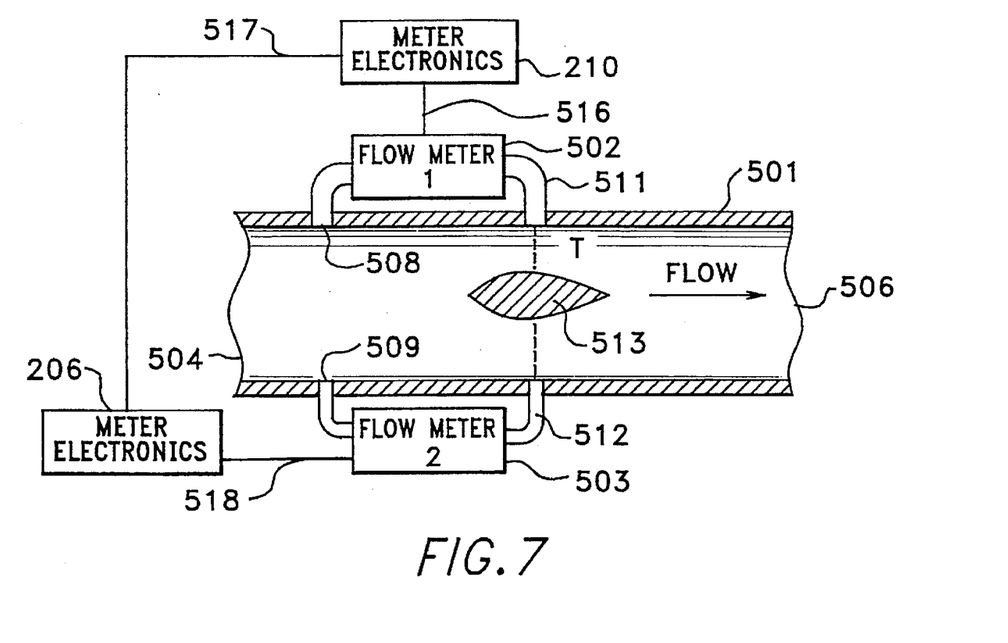
FIG. 7 is similar to FIG. 5 except that the flowmeter inlets are flush with the inner walls of conduit 701.

Description of FIG. 7

FIG. 7 is similar to FIG. 5 except that the inlets 508 and 509 of flowmeters 502 and 503 terminate flush with the inner wall of conduit 501.

Derivation of Viscosity Equation

A mathematical derivation follows which shows how the material viscosity may be derived from the flow rate, density, and velocities of the flowing material. The derivation is based on the geometry shown in FIGS. 1 and 2. The derivation uses the fact that at equilibrium, the pressure driving the material flow through the flow channels is equal to the viscous pressure drop in those channels. The same approach could be used with other similar geometries resulting in a different equation, but still an equation from which viscosity could derived. The critical factor in any geometry is that it must contain two parallel flow paths of unequal resistance to flow.

In order to understand the following description of how the present invention determines material viscosity, it is necessary to define and understand terms such as static, total, and dynamic pressure. Static pressure is the pressure which with we are most familiar. It is the pressure of a static material (air in a tire). Moving material also has a static pressure. The static pressure of moving material in a conduit is measured by orienting the inlet of a pressure gage perpendicular to the direction of motion of the material in the conduit. Facing the gauge inlet upstream in the conduit results in a pressure higher than the static pressure. The difference in pressure between the upstream facing inlet and the static pressure of the perpendicular facing inlet is the dynamic pressure of the material. This dynamic pressure is a measure of the kinetic energy of the material and is represented by the equation:

$$P_d = \frac{\rho V^2}{2} \quad (1)$$

$P_d$=dynamic pressure
$\rho$=material density
V=material velocity

The dynamic material pressure in a conduit can be converted to static pressure by decreasing the material velocity while also avoiding turbulence. This is normally done by way of a long slow taper that increases the diameter of the material conveying conduit and decreases material velocity. An abrupt conduit diameter increase results in the conversion of the kinetic energy into turbulence and heat rather than increased static pressure. This results in a loss in total pressure TP in the conduit.

Static pressure can also be converted into dynamic pressure by reversing the conduit taper so that the conduit diameter gets smaller and the material velocity increases. It is easier to convert static pressure into dynamic pressure than the inverse because the decreasing conduit diameter tends to decrease turbulence and energy loss.

Total pressure, TP, in a conduit is defined as the sum of static pressure Ps and dynamic pressure Pd. The total pressure of flowing material in a conduit can remain constant, by Bernoulii's law, as material pressure is converted between static and dynamic pressure if turbulent and viscous losses are neglected. Turbulent and viscous losses, however, in reality, decrease the total pressure. Viscous losses will be neglected in the first half of the following derivation, but then taken into account in the second half.

FIG. 1 shows a conduit 101 which gradually contracts into a conduit 102 of lesser diameter at B. After a short distance, conduit 102 enlarges at C abruptly into a conduit 103 of the same diameter as conduit 101. A determination of the pressure drop between B and C in terms of the pressures at A and D is useful in determining viscosity. Since the conduit diameters at A and D are the same, the dynamic pressures Pd must also be equal at A and D. Continuity requires that the flow rate at A and D is also equal. This means that the difference in total pressures TP between A and D must be equal to the difference in static pressures between A and D. The same holds true for the points B and C. Note that C-D is an abrupt transition where turbulence is generated and total pressure is lost.

In FIG. 1, the upstream contraction of conduit 101 at B is configured to conserve total pressure TP. Some of the static pressure Ps at A is converted to dynamic pressure Pd at B as the material accelerates into the smaller diameter conduit 102. Thus, the dynamic pressure $P_d$ (kinetic energy) at B is greater than at A. The downstream transition at C-D is abrupt so that the increased kinetic energy (dynamic pressure) of the material in the conduit 102 at C (as compared to that at A) is lost (to turbulence) as it enters the larger diameter conduit 103 and is not converted back to static pressure Ps which is less at D than it is at A. This reduces the static pressure at D as compared to that at A. This lost energy can be quantified by the following equation.

$$\delta P_L = \frac{\rho(V_C^2 - V_D^2)}{2} \quad (2)$$

$\delta P_L$=turbulent pressure loss
$\rho$=material density
$V_C$=material velocity in conduit 102
$V_D$=material velocity in conduit 103

The energy lost is the difference in dynamic pressure between C and D. Instead of being converted back to static pressure at D, as it would with a gradual transition, it is lost as turbulence. This means that the static pressure remains unchanged between C and D while the total pressure decreases by the amount given in equation 2.

$$TP_C = TP_D + \frac{\rho(V_C^2 - V_D^2)}{2} \quad (3)$$

$TP_D$=total pressure at D
$TP_C$=total pressure at C

The total pressure at C is greater than the total pressure at D by an amount equal to the turbulent pressure energy loss. The total pressures at C and D can be represented as the sum of the static and dynamic pressures at each point.

$$P_C + \frac{\rho V_C^2}{2} = P_D + \frac{\rho V_D^2}{2} + \frac{\rho(V_C^2 - V_D^2)}{2} \quad (4)$$

$P_C$=static pressure at C
$P_D$=static pressure at D

Equation 4 can be simplified by cancellation of terms to the following.

$$P_C = P_D \quad (5)$$

Thus it is shown that the static pressure in exit conduit 103 at D is equal to the static pressure at the exit of conduit 102 at C. This static pressure is less than the static pressure at A. The difference is equal to dynamic pressure loss of equation 2.

The static pressure at the inlet B to the conduit 102, can be determined from the total pressure at point A if it is assumed that the transition is short enough that the viscous losses can be neglected, yet gradual enough that energy is not lost to turbulence. The total pressure at A is equal to the total pressure at B from Bernoulli's law.

$$TP_A = TP_B \quad (6)$$

$TP_A$=total pressure at A
$TP_B$=total pressure at B

Substituting static plus dynamic pressures for the total pressure at A & B results in the equation:

$$P_A + \frac{\rho V_A^2}{2} = P_B + \frac{\rho V_B^2}{2} \quad (7)$$

$P_A$=static pressure at A
$P_B$=static pressure at B
$V_A$=material velocity at A
$V_B$=material velocity at B This equation can be simplified to:

$$P_B = P_A + \frac{\rho(V_A^2 - V_B^2)}{2} \quad (8)$$

The static pressure difference between positions B and C, $DP_{B-C}$, can now be determined by subtracting the static pressure values of equations 5 and 8.

$$DP_{B-C} = P_A + \frac{\rho(V_A^2 - V_B^2)}{2} - P_D \qquad (9)$$

FIG. 2 shows a conduit 201 which splits into two conduits 204 and 205 of unequal diameters. Each flow path 204/205 contains a Coriolis meter 202/207 to determine the density and mass flow rate for the material in each conduit. From these parameters the material velocity in each conduit 204/205 can be determined. Downstream of the flowmeters the two conduits 208/209 rejoin into a single conduit D of the same diameter as upstream at A. As before, it is of significance that the upstream divergence at B of the two conduits 204/205 is configured so as to conserve total pressure while the abrupt downstream convergence at C is configured so that the excess kinetic energy of the material in the conduits 208/209 is lost as it enters the larger conduit 203 at D.

The pressure DP driving a material flow through flowmeters 1 and 2 (202 and 207) of FIG. 2, is given by the following equations as in equation 9.

For flowmeter 1

$$DP_1 = P_A + \frac{\rho(V_A^2 - V_1^2)}{2} - P_D \qquad (10.1)$$

$DP_1$=driving pressure drop for flowmeter 1
$P_A$=static pressure at A
$P_D$=Static pressure at D
$V_P$=velocity at A (pipeline)
$V_1$=velocity in flowmeter 1
$\rho$=material density
$V_A$=Velocity at A For Flowmeter 2

$$DP_2 = P_A + \frac{\rho(V_A^2 - V_2^2)}{2} - P_D \qquad (10.2)$$

$DP_2$=driving pressure drop for flowmeter 2
$V_2$=velocity in flowmeter 2

At an equilibrium condition, the pressure driving the material through flowmeters 1 and 2, (equations 10.1 and 10.2) is equal to the pressure drop or resistance to flow in the flowmeters.

$$DP_1 = \delta P_1 \qquad (11.1)$$

$\delta P_1$=pressure drop of flowmeter 1

$$DP_2 = \delta P_2 \qquad (11.2)$$

$\delta P_2$=pressure drop of flowmeter 2

Substituting equation 10.1 and 10.2 into 11.1 and 11.2, and subtracting the kinetic energy term of equations 10 from both sides of this equation results in:

$$P_A - P_D = \delta P_1 - \frac{\rho(V_A^2 - V_1^2)}{2} \qquad (12.1)$$

$$P_A - P_D = \delta P_2 - \frac{\rho(V_A^2 - V_2^2)}{2} \qquad (12.2)$$

These equations can be applied to the two flowmeters of FIG. 2. Since the left sides of both equations 12.1 and 12.2 are the same, the right sides are equal.

$$P_A - P_D = \delta P_1 - \frac{\rho(V_A^2 - V_1^2)}{2} = \delta P_2 - \frac{\rho(V_A^2 - V_2^2)}{2} \qquad (13)$$

The first term, $P_A$-$P_D$, can be dropped and the remaining equation can be simplified to yield:

$$\delta P_1 + \frac{\rho V_1^2}{2} = \delta P_2 + \frac{\rho V_2^2}{2} \qquad (14)$$

The pressure drops, $\delta P_1$, and $\delta P_2$ in flowmeters 1 and 2 which results from the material viscosity can be represented by the Darcey formula. Other pressure drop equations representing other geometries and flow regimes can also be used here without effecting the subsequent solution. The Darcey formula is:

$$\delta P_1 = f_1 \frac{L_1}{d_1} \frac{\rho V_1^2}{2} \qquad (15.1)$$

$f_1$ = flowmeter 1 friction factor
$L_1$ = flowmeter 1 conduit length
$d_1$ = flowmeter 1 conduit diameter
$V_1$ = flowmeter 1 material velocity $$\delta P_2 = f_2 \frac{L_2}{d_2} \frac{\rho V_2^2}{2} \qquad (15.2)$$

$f_2$ = flowmeter 2 friction factor
$L_2$ = flowmeter 2 conduit length
$d_2$ = flowmeter 2 conduit diameter
$V_1$ = flowmeter 2 material velocity $f_1$=flowmeter 1 friction factor
$L_1$=flowmeter 1 conduit length
$d_1$=flowmeter 1 conduit diameter
$V_1$=flowmeter 1 material velocity
$f_2$=flowmeter 2 friction factor
$L_2$=flowmeter 2 conduit length
$d_2$=flowmeter 2 conduit diameter
$V_1$=flowmeter 2 material velocity Substituting equation 15 into equation 14 results in:

$$f_1 \frac{L_1}{d_1} \frac{\rho V_1^2}{2} + \frac{\rho V_1^2}{2} = f_2 \frac{L_2}{d_2} \frac{\rho V_2^2}{2} + \frac{\rho V_2^2}{2} \qquad (16)$$

After canceling density, $\rho$, from both sides, this equation may be simplified to the following:

$$V_1^2 \left( f_1 \frac{L_1}{d_1} + 1 \right) = V_2^2 \left( f_2 \frac{L_2}{d_2} + 1 \right) \qquad (17)$$

Solving for the velocity ratio (squared) of the material in the two conduits results in the following:

$$\frac{V_2^2}{V_1^2} = \frac{f_1 \frac{L_1}{d_1} + 1}{f_2 \frac{L_2}{d_2} + 1} \qquad (18)$$

The friction factors, $f_1$ and $f_2$ can be expanded using the Blasius formula for turbulent flow through a smooth conduit.

$$f_n = \frac{316}{Re^{25}} \qquad (19)$$

Re=Reynolds number
Where:

$$Re = \frac{\rho V d}{\mu} \qquad (20)$$

$\mu$=viscosity

It will be noted here that there are other friction factor algorithms for different flow regimes, surface roughnesses, tube geometries, etc. Any of these based on the Reynolds number or the material viscosity will suffice for the following method of determining viscosity. Substituting equations 19 and 20 into equation 18 results in the following:

$$\frac{V_2^2}{V_1^2} = \frac{\left[\frac{.316}{\left(\frac{\rho V_1 d_1}{\mu}\right)^{.25}}\right]\left(\frac{L_1}{d_1}\right)+1}{\left[\frac{.316}{\left(\frac{\rho V_2 d_2}{\mu}\right)^{.25}}\right]\left(\frac{L_2}{d_2}\right)+1} \quad (21)$$

Since each flowmeter measures its own mass flow and density, its volumetric flow is calculated by dividing mass flow rate by density. The fluid velocity for each flowmeter is then calculated by dividing the volumetric flow rate by the flow channel cross section area. Since the length and diameter of each meter are known constants, all the parameters in this equation except for viscosity are known. In order to reduce the size of the expression in the solution for viscosity, the known parameters are combined into three constants.

$$k_1 = \frac{.316 L_1}{(\rho V_1 d_1)^{.25} d_1} \quad (22)$$

$$k_2 = \frac{.316 L_2}{(\rho V_2 d_2)^{.25} d_2} \quad (23)$$

$$k_3 = \frac{V_2^2}{V_1^2} \quad (24)$$

Substituting equations 22, 23 and 24 into equation 21 results in the following equation.

$$k_3 = \frac{k_1 \mu^{.25} + 1}{k_2 \mu^{.25} + 1} \quad (25)$$

Equation 25 can now be solved for viscosity, resulting in the following equation (26).

$$\mu = \left(\frac{1-k_3}{k_3 k_2 - k_1}\right)^4 \quad (26)$$

Thus it is shown that viscosity can be determined by use of parallel connected flow channels of unequal resistance to flow. The fluid velocity and density of the fluid in each channel is determined by use of a Coriolis meter. This information along with the geometric parameters of the channels is sufficient to calculate viscosity. Modern microprocessors such as presently exist in the electronic controls for Coriolis flowmeters, (such as the Micro Motion RFT9739), are capable of evaluating the above expression and determining fluid viscosity.

It can be seen from equation 21 that a determination of the material viscosity involves a determination of the material velocities in the two flowmeters as represented by the terms on the left and right sides of the equal sign of equation 21. The determination of the material viscosity further involves the flowmeter constants expressed on the right side of the equation 21. These include the length of the flowmeter tubes expressed by $L_1$ and $L_2$ as well as the diameter of the flow tubes expressed by $d_1$ and $d_2$. Each flowmeter in its normal course of operation computes the mass flow rate for the material flowing within it. Each flowmeter also determines the density of the material within it. Thus, the volumetric flow rate for the material is determined by since each flowmeter normally determines both mass flow rate and density. The flow channel area is then used to determine the material velocity which is equal to the volumetric flow rate divided by the cross-sectional area of the flowmeter flow channels. This cross-sectional area information is determined from the terms $d_1$ and $d_2$ in equation 21. These are part of the known flowmeter parameters together with the flow tube lengths $L_1$ and $L_2$.

All of this information regarding the flowmeter parameters is programmed into the meter electronics element 206. Meter electronics 206 receives flow information regarding a first flowmeter from meter electronics 210 and derives flow information for the other flowmeter. In response to the information it stores, receives, and derives element 206 determines mass flow rate and density for the flowing material. Element 206 then uses the flowmeter physical parameters such as length and diameter programmed into it in order to solve equation 25 to derive the viscosity for the material flowing in the flowmeters as well as the viscosity for the material flowing in the conduit when the flowmeter is operated on a bypass basis.

Element 206 may, if desired, comprise a Micro Motion, Inc., model RFT9739 flow transmitter. In accordance with the present invention, the RFT9739 solves equation 25 after being programmed with the constants for each flowmeter such as L1 and L2 as well as in response to the receipt of the output signals from the sensor of each flowmeter in operation. The RFT9739 then operates in response to these signals in pre-programmed information in order to derive the mass flow rate material density, volumetric flow rate, material velocity. Having done this, the RFT9739 then determines the material viscosity.

It is to be expressly understood that the claimed invention is not to be limited to the description of the preferred embodiment but encompasses other modifications and alterations within the scope and spirit of the inventive concept.

The term venturi as used herein may be defined as a section of a flow channel which contains a reduction in flow area followed by a gradual increase in an area such that most of the total fluid pressure is conserved as the static fluid pressure is converted to dynamic pressure and then back to static pressure again.

We claim:

1. Apparatus for determining the viscosity of flowing material; said apparatus comprising:
    a first Coriolis mass flowmeter having an inlet connectable to a material source and an outlet connectable to a material receiver;
    a second Coriolis mass flowmeter having an inlet connectable to said material source and an outlet connectable to said material receiver;.
    said second Coriolis mass flowmeter having a resistance to material flow different in magnitude from a resistance to material flow of said first Coriolis mass flow meter;
    means responsive to a material flow through said first and second Coriolis mass flowmeters from said material source to said material receiver for determining the density and the material flow velocity in said first Coriolis mass flowmeter as well as the density and the material flow velocity in said second Coriolis mass flowmeter; and
    means responsive to said determination of said density and said material flow velocity in each of said first and said second flowmeters for generating output information regarding the viscosity of said flowing material.

2. The apparatus of claim 1 wherein said output information includes the mass flow rate of said material flow.

3. The apparatus of claim 1 wherein said material source comprises a material supply conduit and wherein said material receiver comprises a material receiver conduit;
    means for effectively connecting said inlets of said Coriolis mass flowmeters in parallel with each other to said material supply conduit;

means for effectively connecting said outlets of said Coriolis mass flowmeters in parallel with each other to said material receiver conduit;

means whereby said material flow from said material source conduit to said material receiver conduit via said parallel connected Coriolis mass flowmeters causes said flowmeters to generate information regarding the viscosity of said flowing material.

4. The apparatus of claim 1 wherein said first and second Coriolis mass flowmeters together comprise:

an elongated body;

an upstream end portion of said elongated body comprising an inlet for receiving material to be extended from said material source through said elongated body;

a downstream end portion of said body comprising an outlet for discharging material extended through said elongated body to said material receiver, a pair of flow channels within said body having longitudinal axes substantially parallel to a longitudinal axis of said body;

means connecting downstream ends of said flow channels with said downstream end portion of said body;

means connecting upstream ends of said flow channels with said upstream end portion of said body;

wherein material from said material source enters said inlet of said body and is extended through said flow channels and said outlet of said body to said material receiver;

means for vibrating said flow channels transversely with respect to each other; and means including sensor means responsive to said vibrating while material flows through said flow channels for deriving information, including viscosity, pertaining to said material flow.

5. The apparatus of claim 4 wherein said elongated body is positioned internal to a conduit having a material flow therein and wherein said material source comprises an upstream portion of said conduit and wherein said material receiver comprises a downstream portion of said conduit.

6. The apparatus of claim 4 wherein said inlet of said elongated body is connected to a first conduit comprising said material source and wherein said outlet of said elongated body is connected to a second conduit comprising said material receiver.

7. The apparatus of claim 4 wherein said material source comprises an interior upstream portion of a conduit and wherein said material receiver comprises a downstream portion of said conduit;

said elongated body being positioned external to said conduit;

means for coupling said inlet of said elongated body to material in said upstream portion of said conduit;

means for coupling said outlet of said elongated body to the interior of said downstream portion of said conduit;

wherein material flow through said conduit causes a portion of said material flow to be diverted from said upstream portion of said conduit to said inlet of said elongated body and then be extended through said flow channels of said elongated body and through said outlet of said elongated body to said interior downstream portion of said conduit.

8. The apparatus of claim 7 wherein said interior downstream portion of said conduit includes a venturi means positioned proximate the interior portion of said conduit to which said outlet of said elongated body is coupled;

said venturi means being effective to lower the material pressure within said conduit proximate said outlet.

9. The apparatus of claim 1 wherein said material source comprises an upstream portion of a conduit and wherein said material receiver comprises an interior downstream portion of said conduit;

said first and second Coriolis mass flowmeters being positioned external to said conduit;

means for effectively connecting said inlets of said Coriolis mass flowmeters in parallel with each other to said upstream portion of said conduit;

means for effectively connecting said outlets of said Coriolis mass flowmeters in parallel with each other to said interior downstream portion of said conduit;

whereby said material flow through said conduit causes a portion of said material flow to be diverted from said conduit to said Coriolis mass flowmeters at said upstream portion of said conduit, then to flow through said Coriolis mass flowmeters and be returned to said conduit at said interior downstream portion of said conduit.

10. The apparatus of claim 9 wherein said interior downstream portion of said conduit includes a venturi means positioned proximate the interior downstream portion of said conduit to which said outlets of said of said Coriolis mass flowmeters are coupled;

said venturi means being effective to lower the material pressure of said material proximate said outlets of said Coriolis flowmeter.

11. A method of determining the viscosity of flowing material; said method comprising the steps of:

flowing material through a first Coriolis mass flowmeter having an inlet connectable to a material source and an outlet connectable to a material receiver;

concurrently flowing material through a second Coriolis mass flowmeter having an inlet connectable to said material source and an outlet connectable to said material receiver;

said second Coriolis mass flowmeter having a resistance to material flow different in magnitude from the resistance to material flow of said first Coriolis mass flow meter;

determining the density and the material flow velocity in said first Coriolis flowmeter as well as the density and the material flow velocity in said second Coriolis flowmeter in response to the material flow through said first flowmeter and said second flowmeter; and generating output information regarding the viscosity of said flowing material in response to said determination of said density and said material flow velocity in said first flowmeter and said second flowmeter.

12. The method of claim 11 wherein said output information includes the mass flow rate of said material flow.

13. The method of claim 11 wherein said material viscosity is determined by the steps of:

determining physical parameters of said first and second Coriolis mass flowmeters;

determining the material density, material flow velocity and mass flow rate in said first and second Coriolis mass flowmeters, and determining the ratio of said material flow velocity of said first Coriolis mass flowmeter and the material flow velocity of said second Coriolis mass flowmeter; and determining said material viscosity.

14. The method of claim 11 wherein said material source comprises a material supply conduit and wherein said material receiver comprises a material receiver conduit;

said inlets of said Coriolis mass flowmeters being effectively connectable in parallel with each other to said material supply conduit;

said outlets of said Coriolis mass flowmeters being effectively connectable in parallel with each other to said material receiver conduit;

whereby said material flow from said material source conduit to said material receiver conduit via said parallel connected Coriolis mass flowmeters causes said flowmeters to generate information regarding the viscosity of said flowing material.

15. The method of claim 14 wherein said material viscosity is determined by the steps of:

determining physical parameters of said first and second Coriolis mass flowmeters;

determining the material density, material flow velocity and mass flow rate in said first and second Coriolis mass flowmeters, and determining the ratio of said material flow velocity of said first Coriolis mass flowmeter and the material flow velocity of said second Coriolis mass flowmeter; and determining said material viscosity.

16. The method of claim 11 wherein said first and second Coriolis mass flowmeters together comprise:

an elongated body;

an upstream end portion of said elongated body comprising an inlet for receiving material to be extended from said material source through said elongated body;

a downstream end portion of said elongated body comprising an outlet for discharging material extended through said elongated body to said material receiver, a pair of flow channels within said elongated body having longitudinal axes parallel to a longitudinal axis of said elongated body;

wherein said method further comprises the steps of:

connecting downstream ends of said flow channels with said downstream end portion of said elongated body;

connecting upstream ends of said flow channels with said upstream end portion of said elongated body;

wherein material from said material source that enters said inlet of said elongated body is extended through said flow channels and said outlet of said elongated body to said material receiver;

vibrating said flow channels transversely with respect to each other; and deriving information, including viscosity, pertaining to said material flow in response to said vibrating while material flows through said channels.

17. The method of claim 15 wherein said elongated body is positioned internal to a conduit having a material flow therein and wherein said material source comprises material in a upstream portion of said conduit and wherein said material receiver comprises an internal downstream portion of said conduit.

18. The method of claim 15 wherein said inlet of said elongated body is connected to a first conduit comprising said material source and wherein said outlet of said elongated body is connected to a second conduit comprising said material receiver.

19. The method of claim 15 wherein said material source comprises an upstream portion of a conduit and wherein said material receiver comprises an interior downstream portion of said conduit;

said elongated body being positioned external to said conduit;

said method further comprises the steps of:

coupling said inlet of said elongated body to material in said upstream portion of said conduit; and coupling said outlet of said elongated body to the interior of said downstream portion of said conduit;

wherein material flow through said conduit causes a portion of said material flow to be diverted from said upstream portion of said conduit to said inlet of said elongated body and then be extended through said flow channels of said elongated body and through said outlet of said elongated body to said interior downstream portion of said conduit.

20. The method of claim 19 wherein said interior portion of said conduit includes a venturi means positioned proximate the interior portion of said conduit to which said outlet of said elongated body is coupled;

said venturi means being effective to lower the material pressure within said conduit proximate said outlet.

21. The method of claim 11 wherein said material source comprises an upstream portion of a conduit and wherein said material receiver comprises an interior downstream portion of said conduit;

said first and second mass flowmeters being positioned external to said conduit;

said method further comprising the steps of:

effectively connecting said inlets of said Coriolis mass flowmeters in parallel with each other to said upstream portion of said conduit; and effectively connecting said outlets of said Coriolis mass flowmeters in parallel with each other to said interior downstream portion of said conduit;

whereby said material flow through said conduit causes a portion of said material flow to be diverted from said conduit to said Coriolis mass flowmeters at said upstream portion of said conduit, then to flow through said Coriolis mass flowmeters and be returned to said conduit at said interior downstream portion of said conduit.

22. The method of claim 21 wherein said material viscosity determined by the steps of:

determining physical parameters of said first and second Coriolis mass flowmeters;

determining the material density, material flow velocity and mass flow rate in said first and second Coriolis mass flowmeters, and determining the ratio of said material flow velocity of said first Coriolis mass flowmeter and the material flow velocity of said second Coriolis mass flowmeter; and determining said material viscosity.

23. The method of claim 21 wherein said interior downstream portion of said conduit includes a venturi means positioned proximate the interior downstream portion of said conduit to which said outlets of said of said Coriolis mass flowmeters are coupled;

said venturi means being effective to lower the material pressure within said conduit proximate said outlets.

* * * * *